(12) United States Patent
Kim et al.

(10) Patent No.: US 6,998,120 B2
(45) Date of Patent: *Feb. 14, 2006

(54) DUAL ROLES OF PEPPER ESTERASE AS A BIOCONTROL AGENT

(75) Inventors: Young Soon Kim, Kwangju (KR); Hyo Hyoun Seo, Kwangju (KR); Moon Kyung Ko, Suncheon-Shi (KR); Boung-Jun Oh, Kwangju (KR); Pill-Soon Song, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 81 days.

This patent is subject to a terminal disclaimer.

(21) Appl. No.: 10/848,375

(22) Filed: May 19, 2004

(65) Prior Publication Data

US 2005/0260184 A1    Nov. 24, 2005

(51) Int. Cl.
*A61K 38/46* (2006.01)
*C12N 9/16* (2006.01)
*C12N 9/20* (2006.01)
*C12N 1/20* (2006.01)
*C12N 15/00* (2006.01)

(52) U.S. Cl. .................. 424/94.6; 435/196; 435/198; 435/252.3; 435/320.1; 536/23.2; 530/350

(58) Field of Classification Search ............ 435/196, 435/198, 252.3, 320.1; 536/23.2; 530/350; 424/94.6

See application file for complete search history.

(56) References Cited

U.S. PATENT DOCUMENTS 6,252,049 B1 * 6/2001 Oh et al. .............. 530/370

OTHER PUBLICATIONS

Kim et al. Molecular Plant-Microbe Interaction, vol. 14(1): 80-85 (Jan. 2001).*

Baudouin et al.; Eur. J. Biochem. 248, 700-706, 1997: *Functional expression of a tobacco gene related to the serine hydrolase family.*

Carvalho, et al.; EJB Electronic Journal of Biotechnology ISSN:0717-345, vol. 1, No. 3, 1998: *Cutinase structure, function and biocatalytic applications.*

Warm et al.; PHYTOCHEMISTRY, vol. 21, No. 4, pp. 827-831, 1982: *Quantification of Hydrogen Peroxide in Plant Extracts by the Chemiluminescence Reaction with Luminol.*

Falk et al.; Proc. Natl. Acad. Sci. USA, vol. 96, pp. 3292-3297, Mar. 1999, Plant Biology: *ESD1, an essential component of R gene-mediated disease resistance in Arabidopsis has homology to eukaryotic lipases.*

Fauth, et al..; Plant Physiol. (1998) 117:1373-1380: *Cutin Monomers and Surface Wax constituents Elicit $H_2O_2$ in Conditioned Cucumber Hypocotyl Segments and Enhance the Activity of Other $H_2O_2$ Elicitors.*

Jirage, et al.: PNAS, vol. 96, No. 23, 13583-13588, 1999: *Arabidopsis thaliana PAD4 encodes a lipase-like gene that is important for salicyclic acid signaling.*

Oh, et al.; J. Phytopathology 146, 301-303, 1998: *A Microscopic Characterization of the Invection of Green and Red Pepper Fruits by an Isolate of Colletotrichum gloeosporioides.*

Schweitzer et al.; The Plant Journal (1996) 10(2), 331-341: *Perception of free cutin monomers by plant cells.*

* cited by examiner

*Primary Examiner*—Tekchand Saidha
(74) *Attorney, Agent, or Firm*—Kenyon & Kenyon

(57) ABSTRACT

This invention relates to dual roles of the pepper esterase protein as a biocontrol agent that can elicit defense reactions in plant cells and as direct fungal inhibitor that can block fungal penetration into plant cells. The possible enzymatic actions of the PepEST protein were elucidated in both fungus and plant to gain insight into the molecular mechanisms involved in the fungal resistance. Exogenously treated PepEST protein on the unripe pepper fruits decomposed the cuticles of the fruits and released glycerol and 9-octadecenamide. The treatment resulted in the massive generation of hydrogen peroxide in the unripe pepper fruit and simultaneously elicited the expression of defense-related genes in both absence and presence of the fungus.

3 Claims, 12 Drawing Sheets

A.

B.

SEQUENCE LISTING

```
<160> NUMBER OF SEQ ID NOS: 10

<210> SEQ ID NO 1
<211> LENGTH: 328
<212> TYPE: PRT
<213> ORGANISM: Capsicum annuum

<400> SEQUENCE: 1

Met Ala Ser Gln Ser Phe Val Pro Pro Ile Phe Glu Asn Pro Phe Leu
 1               5                  10                  15

Asn Ile Glu Glu Leu Ala Gly Asp Thr Ile Val Arg Lys Pro Glu Pro
             20                  25                  30

Leu Thr Gln Ala Asn Ser Asp Pro Asn Gly Thr Ser Leu Val Val Ser
         35                  40                  45

Lys Asp Val Asp Leu Asp Ile Asn Lys Lys Thr Trp Leu Arg Ile Tyr
     50                  55                  60

Val Pro Gln Arg Ile Ile Thr Asn His Asn Asp Asp Glu Lys Leu Pro
 65                  70                  75                  80

Val Ile Phe Tyr Tyr His Gly Gly Phe Val Phe His Ala Asn
                 85                  90                  95

Ser Phe Ala Trp Asp Leu Phe Cys Gln Gly Leu Ala Gly Asn Leu Gly
                100                 105                 110

Ala Met Val Ile Ser Leu Glu Phe Arg Leu Ala Pro Glu Asn Arg Leu
            115                 120                 125

Pro Ala Ala Tyr Asp Ala Met Asp Asp Gly Leu Tyr Trp Ile Lys Ser
    130                 135                 140

Thr Gln Asp Glu Trp Val Arg Lys Tyr Ser Asp Leu Ser Asn Val Tyr
145                 150                 155                 160

Leu Phe Gly Ser Ser Cys Gly Gly Asn Ile Ala Tyr His Ala Gly Leu
                165                 170                 175

Arg Val Ala Ala Gly Ala Tyr Lys Glu Leu Glu Phe Val Lys Ile Lys
            180                 185                 190

Gly Leu Ile Leu His Gln Pro Tyr Phe Ser Gly Lys Asn Arg Thr Glu
        195                 200                 205

Ser Glu Glu Lys Leu Lys Asp Asp Gln Leu Leu Pro Leu His Ala Ile
    210                 215                 220

Asp Lys Met Phe Asp Leu Ser Leu Pro Lys Gly Thr Leu Asp His Asp
```

-continued

```
            225                 230                 235                 240
    His Glu Tyr Ser Asn Pro Phe Leu Asn Gly Gly Ser Lys His Leu Asp
                    245                 250                 255
    Asp Val Ile Ala Gln Gly Trp Lys Ile Leu Val Thr Gly Val Ser Gly
                260                 265                 270
    Asp Pro Leu Val Asp Asn Ala Arg Asn Phe Ala Asn Phe Met Glu Glu
                275                 280                 285
    Lys Gly Ile Lys Thr Phe Lys Leu Phe Gly Asp Gly Tyr His Ala Ile
                290                 295                 300
    Glu Gly Phe Glu Pro Ser Lys Ala Ala Leu Ile Gly Ala Thr Lys
    305                 310                 315                 320
    Asp Phe Ile Cys Ala Thr Thr Asn
                    325

<210> SEQ ID NO 2
<211> LENGTH: 1217
<212> TYPE: DNA
<213> ORGANISM: Capsicum annuum

<400> SEQUENCE: 2
ttatctgtgt gatcaattat tatggctagc caaagttttg ttcctccaat ttttgaaaat      60
ccctttctta acattgaaga attagcaggt gacacaattg tacgtaaacc tgaacccctc     120
acacaagcca attctgatcc caatggcacg tccttagttg tatctaaaga cgtagacctt     180
gacatcaaca aaaagacatg gctgcgaata tacgtcccac aacgaataat cacaaatcat     240
aatgatgatg aaaaattgcc tgtcattttc tactaccatg gtggaggctt tgttttcttc     300
catgccaata gttttgcctg ggatttgttt tgtcaaggac ttgctggaaa ccttggggca     360
atggttatct cccttgaatt tcgtctggcc cctgaaaatc gccttcctgc agcttacgac     420
gatgccatgg atgggttata ttggattaaa tcaactcaag atgaatgggt ccgaaaatat     480
tcagatttga gtaacgttta tcttttttgga tctagttgcg gtggaaacat agcttaccat     540
gcagggttac gggtagcagc tgggcatat aaagaactag agccagtgaa gatcaaaggg     600
ctaattttgc atcaaccata tttcagtgga aaaaacagga cagaatctga agagaagcta     660
aaggatgatc aacttttgcc attacatgca attgacaaaa tgttcgactt gtccttgcca     720
aaagggacac ttgatcatga tcatgaatat tccaatccat ttcttaatgg agggtccaag     780
catttagatg atgtgatcgc acaaggctgg aagattcttg taactggtgt ctctggagat     840
cctctggttg ataatgcgcg caactttgca aattttatgg aagaaaaagg cataaaaact     900
ttcaagctct ttggagatgg ttatcatgca attgagggt ttgaaccatc aaaggcagca     960
gctttaattg gcgccaccaa agatttcata tgtgctacta caaattaaaa atatgtaacg    1020
tagcatcctg ctagcgttgt gtttgtttca tttccttcaa ataaatcaag tgagcttctt    1080
tgtgcaaata agagggttt acaccctcct cctgttaga gattactta aatattata       1140
tttctcttga agatcaaagt tttagagatg agttattgct gaaaaaaaa aaaaaaaaa    1200
aaaaaaaaaa aaaaaa                                                 1217

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
```
atggagttct ctgtatcacc agtgg                                              25

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tccgaatgtc taaagtggta caag                                               24

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
atgggctatt tgagatcatc t                                                  21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tcacctctct gcaatcaata t                                                  21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ctgacaagtc cacagcctca g                                                  21

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
gttctttcca tgacaaccaa ttg                                                23

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gggggatcca aaatggctcg ttcc                                               24

<210> SEQ ID NO 10
<211> LENGTH: 33
<212> TYPE: DNA

```
-continued

<213> ORGANISM: Artificial Sequence
<220> FEATURE:
<223> OTHER INFORMATION: primer

<400> SEQUENCE: 10
ctcggtaccc tttatttaat tttgtgtgac act                              33
```

DUAL ROLES OF PEPPER ESTERASE AS A BIOCONTROL AGENT

FIELD OF THE INVENTION

This invention relates to a pepper esterase (PepEST) recombinant protein as a biocontol agent, more particularly, relates to dual roles of the recombinant protein as a biocontrol agent that can elicit defense reactions in plant cells and as direct fungal inhibitor that can block fungal penetration into plant cells.

BACKGROUND OF THE INVENTION

Plants have evolved an array of cellular mechanisms to defend themselves against invading pathogens. Upon recognition of pathogens, plants activate a complex set of defense reactions to reject pathogen attack. It includes acute defense at the infection site following sometimes by induction of immunity at distal plant parts. Development of resistances at local and distal sites is associated in part with the expression of anti-microbial proteins. Those include glucanases, chitinases, and lysozymes deposited in the plants that are exhibiting increased resistance to various microorganisms. Recently, anti-microbial proteins had been introduced into crop plants in order to control phyto-pathogens. Particularly, the antifungal polypeptide can be applied directly onto susceptible plants to provide protection against fungus.

*Colletotrichum gloeosporioides* (Penz.) is the casual agent of anthracnose diseases, which is the most destructive disease in worldwide grown pepper. Nowadays anthracnose fungus is mainly controlled by application of substantial amounts of chemicals. To limit agro-chemicals in crop cultivation, there is an urgent need for the establishment of resistant pepper cultivars for anthracnose disease. However, classical breeding is not applicable for the development of resistance line, since there is no available genetic resource for the disease resistance. At present, all commercial pepper lines are still susceptible to anthracnose disease.

In pepper, plant responses to fungal morphogenesis are different dependent on the ripening stage of pepper fruits. Disease symptoms are developed in the unripe fruit, but not in the ripe fruits infected with anthracnose fungus. To gain genetic resources responsible for the resistance, several genes were previously isolated from the ripe fruit interacting with anthracnose. Among them, a pepper esterase gene (PepEST) encoding a member of esterase family showed an antifungal activity against anthracnose fungus and rice blast fungus. In this invention, the mode of the enzymatic action of PepEST protein was elucidated to gain an insight into the molecular mechanisms involved in the resistance reaction in pepper and fungus. PepEST protein was externally applied to induce defense reaction in the unripe fruit and to block fungal penetration into fruit epidermis.

Genetic engineering techniques are offering relief from fungal pathogens through the development of fungus control systems based on PepEST gene, which was isolated by the inventors and was disclosed in U.S. Pat. No. 6,018,038. First is the development of new fungicides using genetically engineered protein. This idea has been already disclosed in U.S. Pat. No. 6,613,323 by the inventors themselves. The second type of application is applying the protein to plants to elicit defense reactions, such as $H_2O_2$ production and PR gene expressions, and to block fungal penetration into plant cells.

The plant cuticle is a physical barrier composed of polyesters of $C_{16}$ and $C_{18}$ hydroxy fatty acids. Infection of *C. gloeosporioides* is achieved through conidium germination and appressorium formation that are necessary for subsequent cuticular penetration. The penetration of fungus into plants is associated with cutinases that hydrolyse plant cuticles. Degradation products of plant cuticles by cutinases serve as chemical signals for activating cutinase gene of fungus. Also, cutin monomers can act to induce resistance in plants against fungal infection. Spray application of $C_{18}$ family of cutin monomers protected barley and rice against phytopathogenic fungi, *Erysiphe gramis* f. sp. Hordei and *Magnaporthe grisea* infection, repectively. Particularly, cutin monomers were reported as the elicitor of $H_2O_2$ and the enhancer of other $H_2O_2$ elicitors in plants. In the present work, we hypothesize that exogenous treatments of a pepper esterase would liberate cutin monomers that can elicit the generation of $H_2O_2$. Then, plant defense genes induced by $H_2O_2$ are deployed for plant protection against fungus.

Ultimately, application of PepEST proteins can provide agromonically relevant level of disease control on pepper cultivation without harmful side effects so as to contribute to more sustainable agricultural practices.

SUMMARY OF THE INVENTION

The object of the present invention is to provide a biocontrol agent comprising the effective amount of pepper esterase (PepEST) having amino acid sequence of SEQ ID NO: 1, wherein said effective amount of pepper esterase is 0.05~0.2 mg per mililiter. The invention relates to the use of the protein with resistance activation in plant. The use means in this context that the formula containing PepEST protein with pathogen controlling action is topically applied to the plant from outside. PepEST protein has primarily decomposed the component of cuticles on pepper fruits. A cutin monomer, 9-octadecenamide, was released from the cuticle. Then, hydrogen peroxide was generated in the unripe fruits where several defense-related genes were subsequently expressed. So, said pepper esterase has the functions for protecting the plant by inducing defense reaction. In this case, said plant is pepper. Further, said pepper esterase dissolves fungal wall, so dithian compound was released from fungus. In addition, the formula containing dithiothreitol (DTT) and the protein fractions showed direct antifungal functions according to the concentrations of said esterase, i) inhibiting the germination of fungal spores; ii) inhibiting fungal penetration into pepper fruits.

For the application of pepper esterase, said fungus is *Colletotrichum gloeosporioides*.

The present invention also provides a formula containing DTT and partially purfied pepper esterase which is produced by transformed *E. coli* harboring the vector containing the cDNA fragment of SEQ ID NO: 2.

DETAILED DESCRIPTION OF THE INVENTION

Carboxylesterases are enzymes that catalyze the hydrolysis of compounds containing an ester bond. In plant-microbe interactions, a tobacco esterase and two *Arabidopsis* lipase genes had been isolated in a hypersensitive reaction against phyto-pathogen. A pepper esterase gene (PepEST) that is highly expressed during the incompatible interaction between the ripe fruit and *C. gloeosporioides* were cloned from pepper. The recombinant PepEST protein expressed in *E. coli* (FIG. 1A) hydrolyzed p-nitrophenyl esters but did not show detestable level of lipase activity.

Since natural substrates for plant esterase are not identified yet, little is known about physiological role of the protein in resistance mechanism of the ripe pepper fruits. Identification of compounds generated by PepEST will help clarify the role of plant esterases in the defense system. So, the effect of PepEST proteins by exogenous treatment was observed on the unripe pepper fruits in terms of resistance induction. In the present work, PepEST protein was shown to sufficient to stimulate a complex defense response in pepper cells comprising the release of cutin monomer, $H_2O_2$ generation, and defense-related gene activation. The results suggest that PepEST gene product is involved in a defense mechanism against the fungal invasion in outer-epidermal cells of the ripe fruits.

Figure 2:
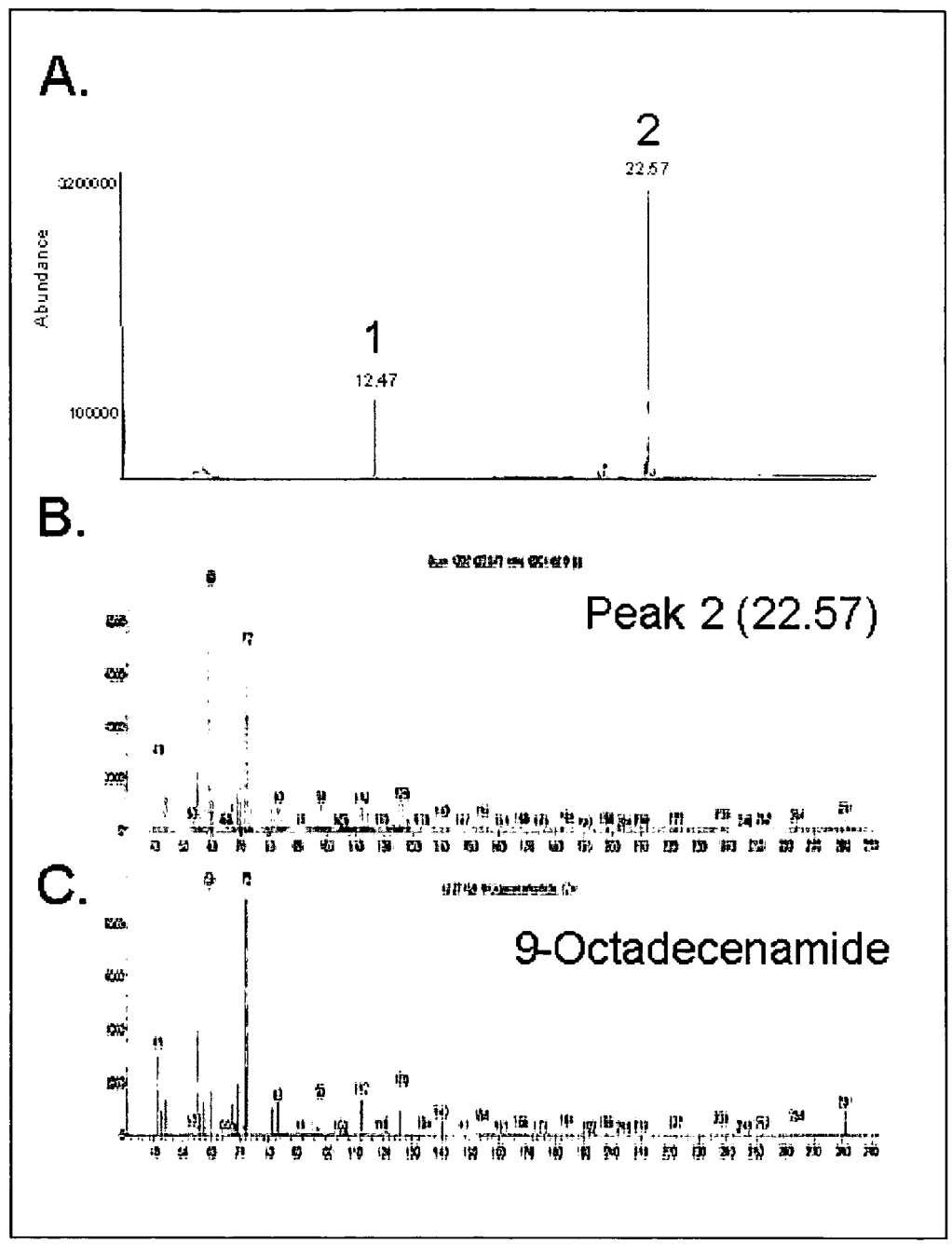
FIG. 2 shows GC-Mass analysis of hydrolyzed materials from the unripe pepper fruit after PepEST treatment (0.1 mg/ml). GC profile (A); Mass spectrum of peak 2 at 22.57 min (B); authentic 9-octadecenamide (C)

Active oxygen species (AOS) have been found to play a number of critical roles in defense responses during plant-pathogen interactions. They can function as messengers for activation of defense response genes beside the direct antimicrobial effect of AOS. We used the unripe pepper fruit to correlate biochemically oriented elicitor experiments. A cutin monomer, 9-octadecenamide, was released from the cuticle of the fruit when PepEST protein was topically applied on the unripe pepper fruit (FIG. 2).

Figure 3:
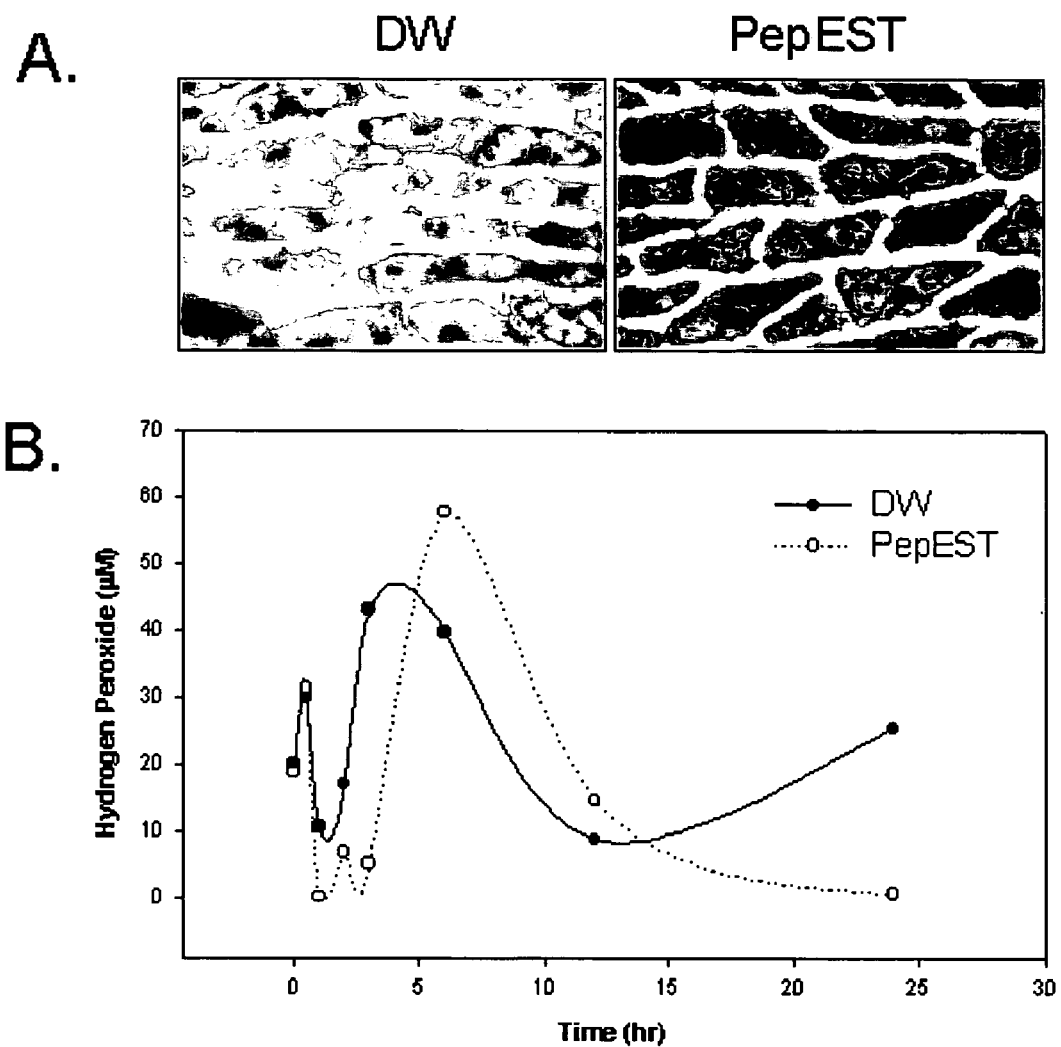
FIG. 3 shows the generation of hydrogen peroxide by exogenous treatment of PepEST protein in pepper. Epidermal cells of the unripe fruit were stained for $H_2O_2$ using diamino-benzidine (DAB) after treatment with 1 μg of PepEST (A); Time course of $H_2O_2$ accumulation in the unripe fruits after 1 μg of PepEST treatment (B).
Figure 4:
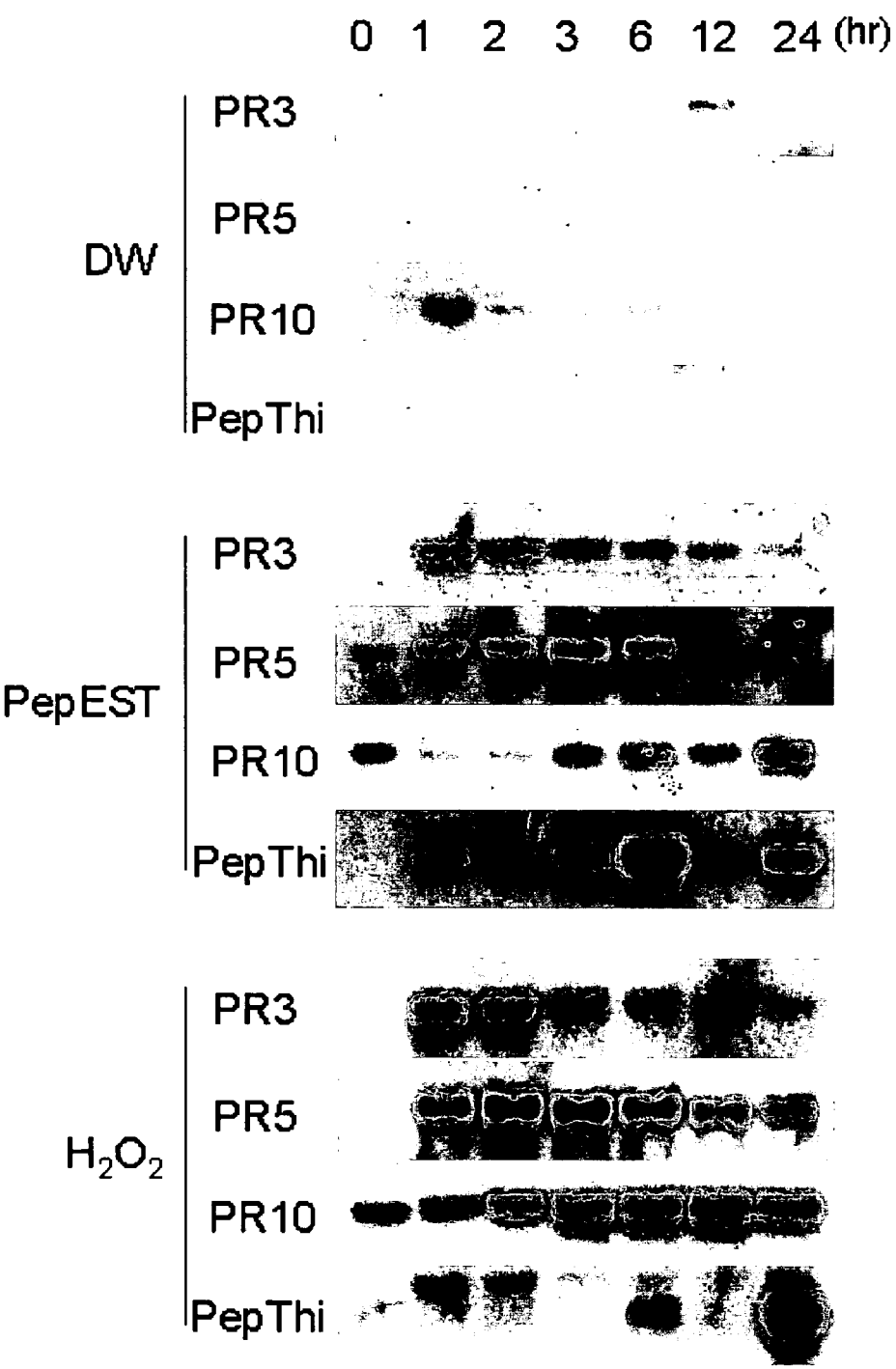
FIG. 4 shows the induction of PR gene expressions in the unripe fruits after treatment with 1 μg of PepEST protein.
Figure 5:
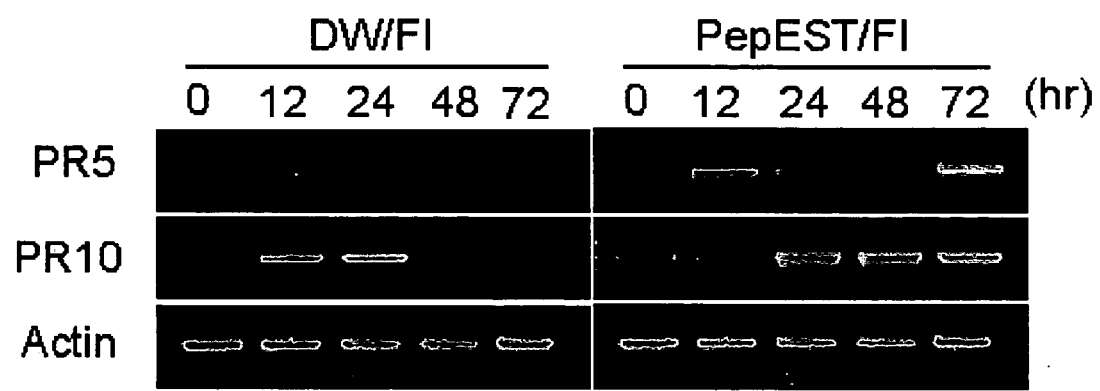
FIG. 5 shows the induction of PR gene expressions by 1 μg of PepEST treatment in the unripe fruit infected with anthracnose fungus.

In addition to cutin monomer solubilization, $H_2O_2$ elicitation was also enhanced by the PepEST protein. In the unripe fruits, $H_2O_2$ generation was doubled at distinct timepoints (6 h) (FIG. 3). Since it could function as activator of defense-related genes as suggested by Iiyama et al (1994), the expression of defense-related genes was determined in pepper after the treatment. Several pepper PR genes were induced by exogenous application of PepEST protein on the unripe fruits (FIG. 4). The expression patterns were similar to those by exogenous $H_2O_2$ treatment. Apparently, $H_2O_2$ modulation can lead to enhanced disease resistance without significant negative effects. Of particular interest in this respect is the observation that $H_2O_2$ modulation is also activated by PepEST treatment during the invasion of the fungus into pepper cells (FIG. 5). PR genes were locally induced in the infection site by adjacent application of PepEST protein with fungal spore on the unripe fruits. Taken together, these results suggest that the PepEST gene as an esterase is involved in the defense response mechanism for the ripe fruit against pathogens.

Figure 6:
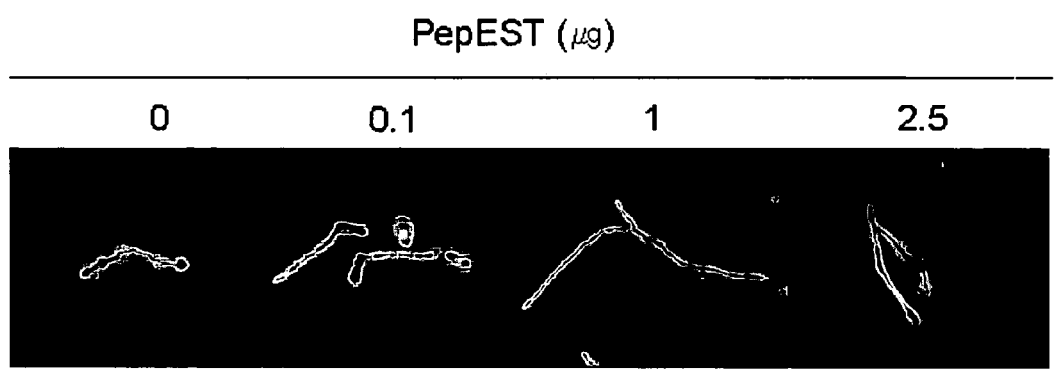
FIG. 6 shows the loss of fungal viability after treatment with PepEST protein.
Figure 7:
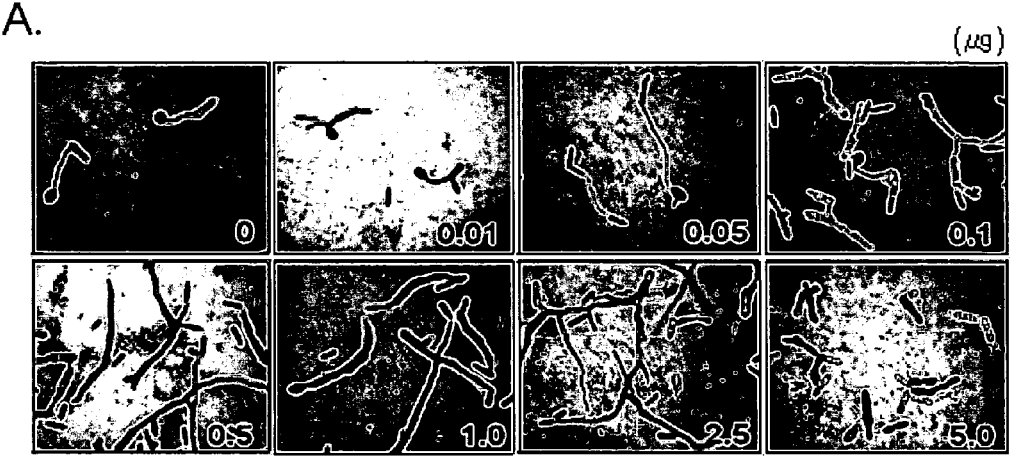
FIG. 7 shows the abnormal growth of fungal development by various concentrations of PepEST protein. The numbers represent the amount of the protein (μg) (A). The inhibition of anthracnose fungus on the unripe pepper fruit after PepEST treatment (B)
Figure 7:
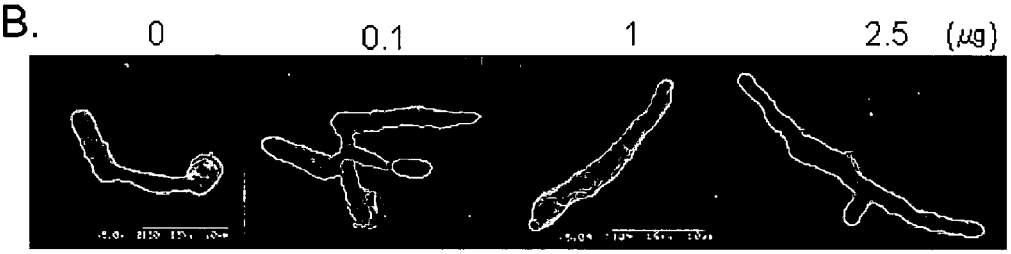
Figure 8:
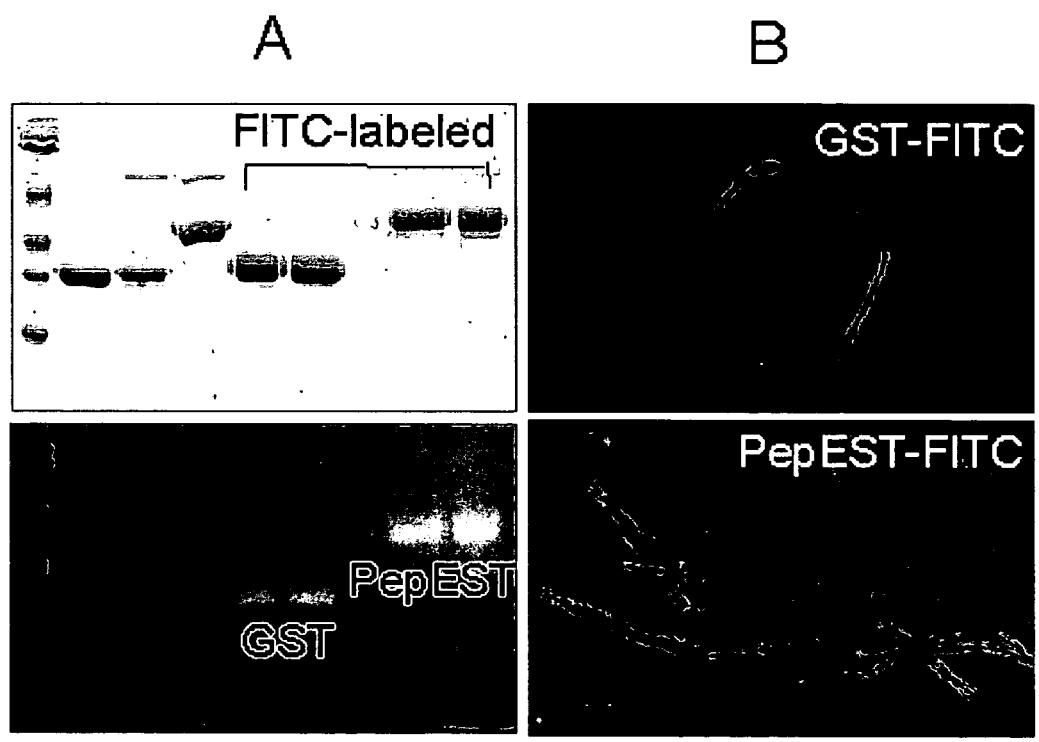
FIG. 8 shows the FITC-labelling of PepEST recombinant protein (A) and attachment of the labeled protein on the surface of the fungus (B).
Figure 9:
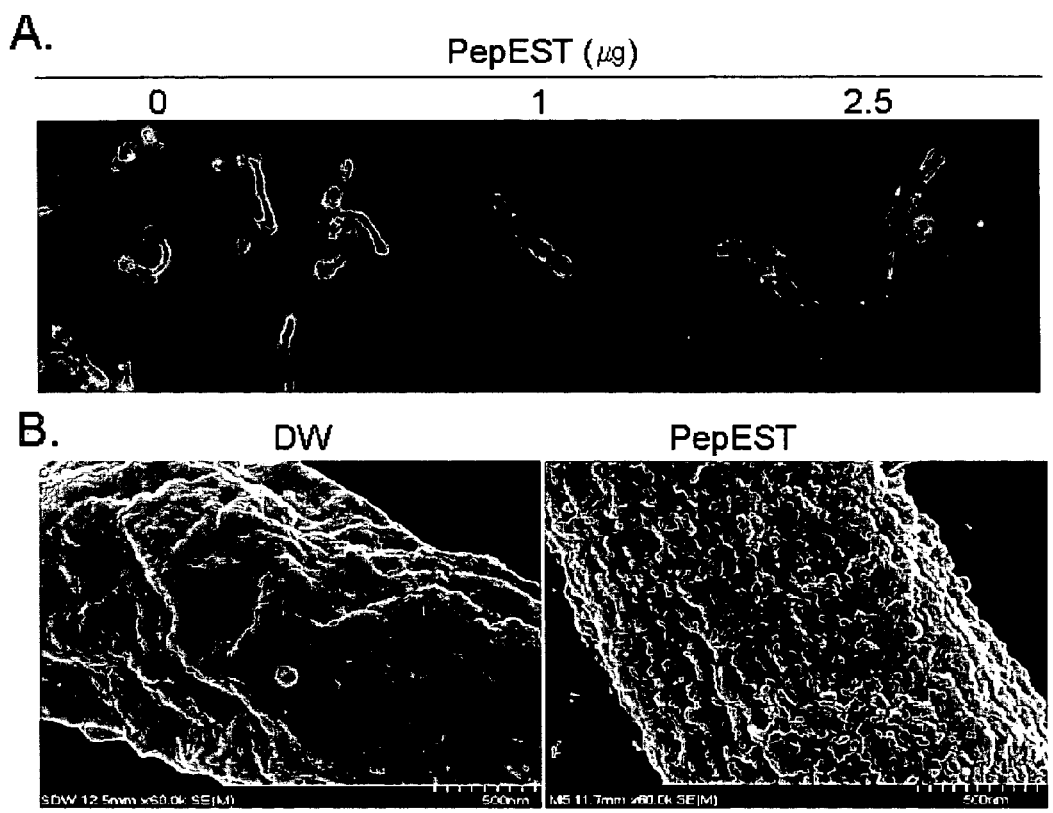
FIG. 9 shows the surface damage of the fungus after treatment with PepEST protein. FITC-labeled Concavanalin A bound to sugar residues on cell surface (A) and the ultrastructure of fungal surface degraded by 1 μg of PepEST treatment (B).
Figure 10:
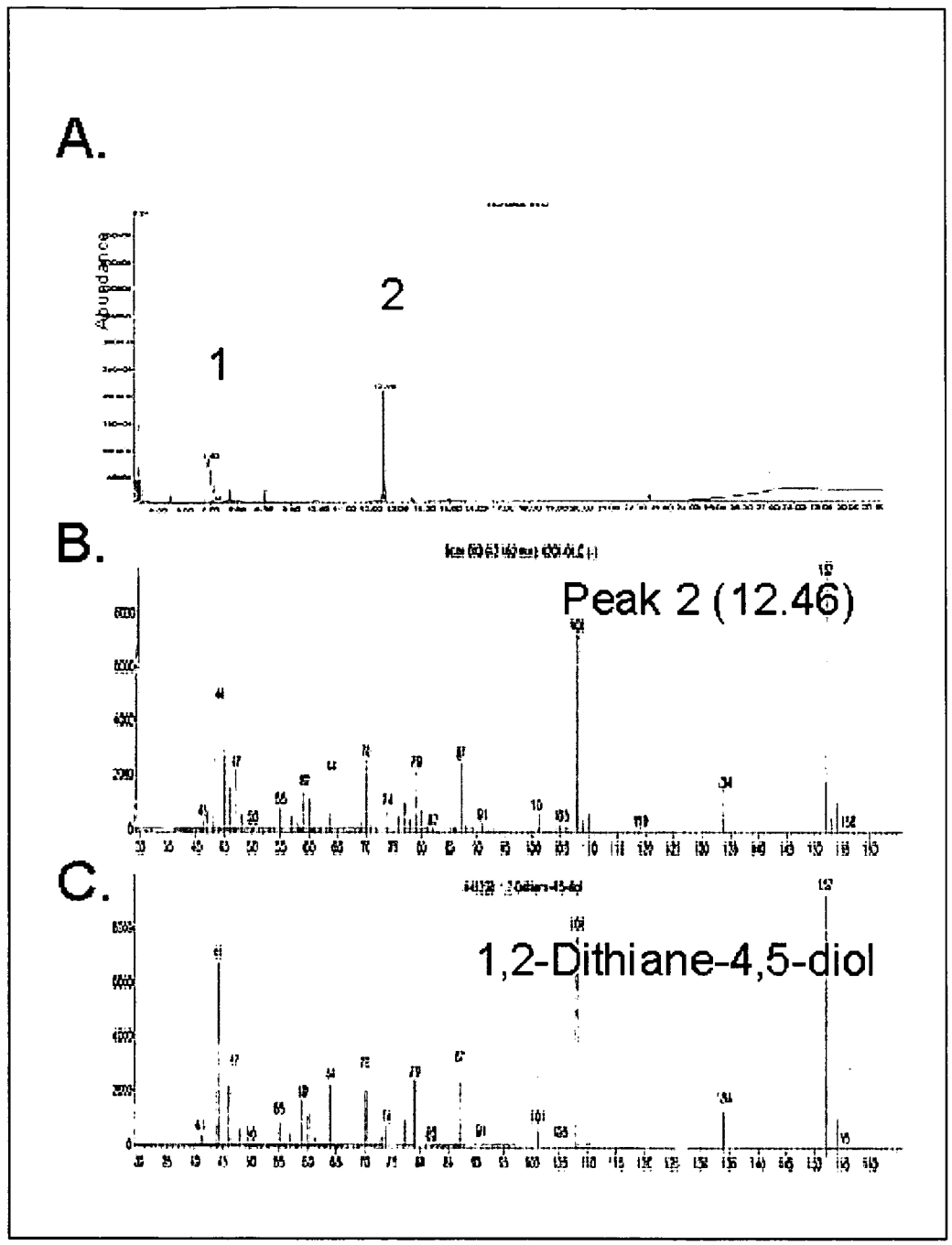
FIG. 10 shows GC-Mass analysis of hydrolyzed materials from anthracnose fungus after PepEST treatment. A, GC profile; B, Mass spectrum of peak 2 at 12.46 min; C, Mass spectrum of authentic 1,2-dithiane-4,5-diol.

On the other hand, the viability of the fungus was severely impaired by PepEST treatment even when the fungal hypha was still elongated (FIG. 6). Ultimately, PepEST protein could inhibit fungal development with mild fungicidal activity so that fungal colonization was completely blocked from the initial infection stage (FIG. 7B). To elucidate the important role of PepEST protein in fungal morphogenesis, we analyzed the walls from germinated conidia of anthracnose fungus treated with PepEST recombinant protein (FIG. 8). The surface of fungus was observed by using FITC-labeled Concanavalin A (Con A), which binds to the sugar residues on the cell wall (FIG. 9A). Unlike normal fungus, the surface of the cell wall treated with PepEST was perturbed when probed with ConA-FITC. In the next to determine whether PepEST hydrolyzes the cell walls, the structure of the walls was observed by using a scanning electron microscope (FIG. 9B). The surface of the fungal cell walls was covered with undefined mucilage materials in distilled water, but the skeletons of the cell wall structure were exposed by enzymatic action of PepEST protein. The results strongly suggest that PepEST protein can hydrolyze the materials covering the fungal walls. Finally, a dithiane compound, 1,2-dithiane-4,5-diol, was detected with glycerol in the solutions from PepEST-treated fungal cell walls (FIG. 10).

Figure 11:
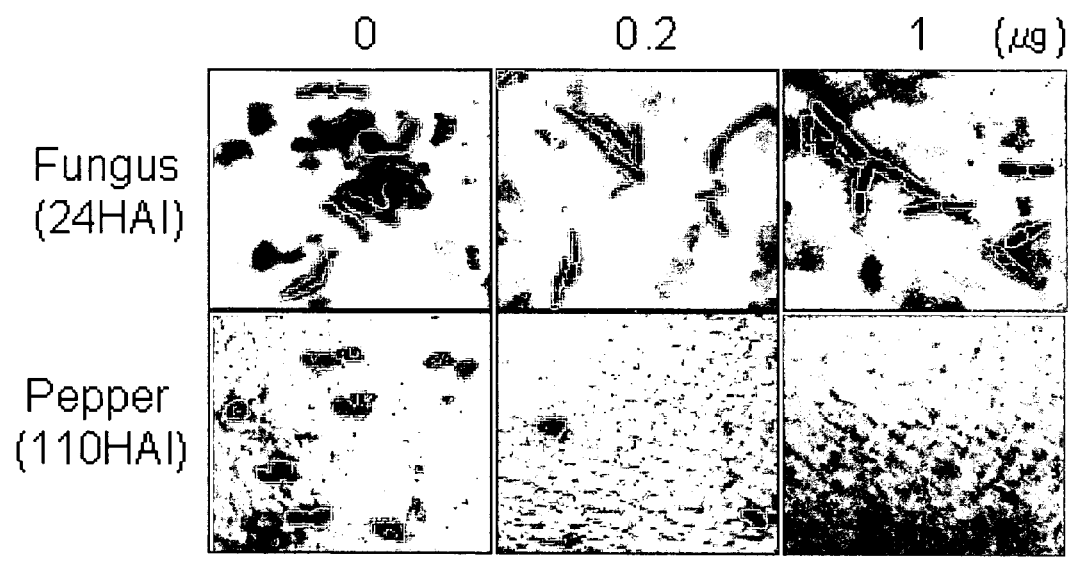
FIG. 11 shows the protection of pepper cells from anthracnose fungus by PepEST protein. Inoculated fruit was photographed at 24 hours after infection (HAI) and 110 hours after infection (HAI) focusing on fungus and pepper epidermis, respectively.
Figure 12:
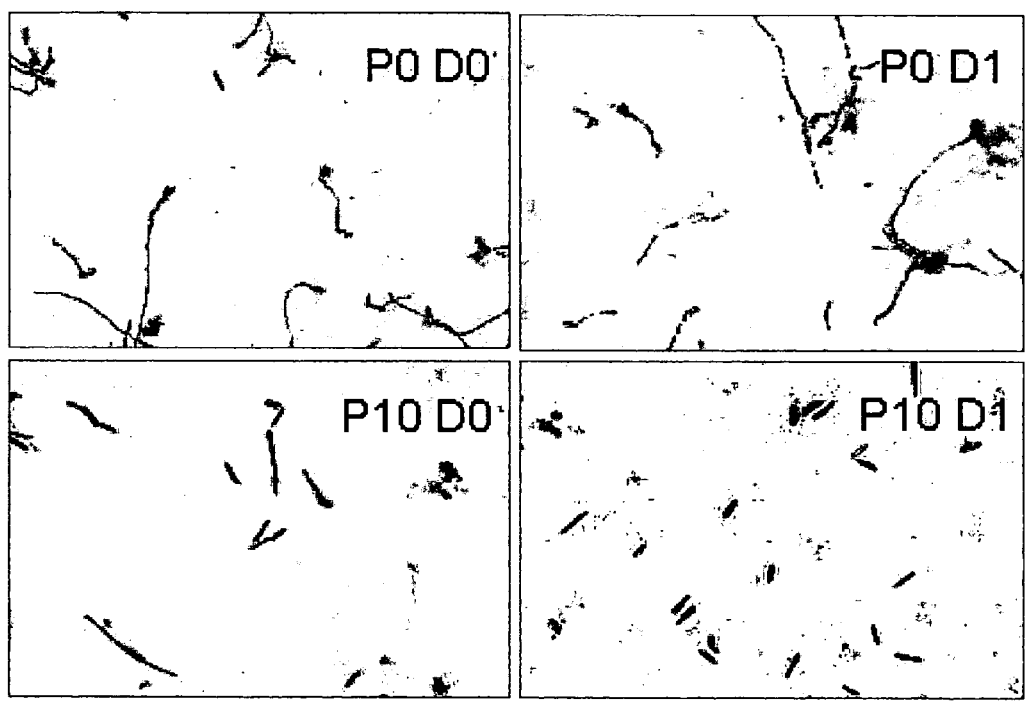
FIG. 12 shows the inhibition of fungal development by a formula containing PepEST protein. The formula contains DTT and PepEST fractions among the soluble proteins of *E. coli* harboring pGEX6p-1/PepEST.

In conclusion, the pepper esterase (PepEST) protects the susceptible unripe fruit against fungal infection by eliciting $H_2O_2$ generation and subsequently inducing the expression of defense-related genes (FIG. 11). It was shown that the pepper esterase can hydrolyze the parts of plant cells as well as the surrounding cell layer of fungus. These results indicate that PepEST protein can be used for disease control as an effective biocontrol agent (FIG. 12). Application of PepEST protein in pepper plants will benefit not only farmers by cutting their cultivation cost but also the environment by reducing the amount of pesticides used.

1. Fungal Inoculums and Plant Material

Monoconidial isolate KG13 of *C. gloeosporioides* was cultured on potato dextrose agar (PDA) (Difco) for 7 days in darkness at 28° C. Conidia were harvested and suspended in sterile distilled water. Ten microliters of spore suspension ($5 \times 10^5$ spores/ml) were used for drop inoculation in vitro and in vivo and amended with 10 µl (final concentration of 1 µg) of recombinant PepEST and applied to cover glasses. As control, 1 µg of GST or sterile water was used. The cover glasses were incubated in humidified chamber at 25° C. in the dark. Then, the spore suspension was stained with 0.1% (wt/vol) cotton blue in lactophenol. Spore germination and appressorium formation on the cover glass were observed under a light microscope (Olympus).

Dosage-response experiments of recombinant PepEST on fungal morphogenesis were performed. Inoculation tests with spores amended with recombinant PepEST per were performed on healthy unripe fruits as previously described (Oh et al., 1998). The fruits were then placed in plastic boxes (25×16×6 cm) containing wet paper towels to maintain 100% relative humidity in darkness at 28° C. After incubation, the fruits were excised to 1 $cm^2$ at the drop-application site for the fungus. The samples were then frozen in liquid nitrogen.

Unripe mature-green pepper fruits were obtained from pepper plants under greenhouse conditions grown at Gwangju, Korea.

2. Solubilization of Surface Wax from Pepper and Fungus by PepEST

10 µl of PepEST protein (0.1 mg/ml) was applied topically on the unripe pepper fruit. The spores were amended with 1 µg of PepEST protein in 10 µl of distilled water. After 24 hrs of treatment, the soluble fraction was collected, lyophilized, and finally dissolved in chloroform. The wax extract was analyzed by GC-mass spectrometry (Hewlett Packard).

3. Quantification of Hydrogen Peroxide 1 g of pepper fruits were frozen in liquid nitrogen and ground to powder in a mortar together with ice-cold 5% TCA and 45 mg of activated charcoal. The powder was centrifuged at 18000 g for 10 min at 0° C. and the supernatant was immediately filtered (Advantec 0.45 µm) under pressure from a syringe to remove any traces of precipitated protein and activated charcoal. The filtrate was adjusted to pH 8.4 with $NH_4OH$ then refiltrate to remove the precipitate, which formed when extracts were neutralized. The amount of $H_2O_2$ in the resulting extract was tested by pipetting 100 µl test solution into 100 µl of 0.5 mM luminol (3-aminophthalhydrazide, Sigma) in 0.2M $NH_4OH$ (pH 9.5). The test tube was placed in a measuring cuvette of Aminco Chem Glow Photometer for chemiluminescence (CL) emission initiated by injecting 100 µl of 1 mM $K_3Fe(CN)_6$ (in 0.2M $NH_4OH$) into the mixture. The emitted photons were counted for 5 sec with a pulse integrator (Lumat LB9501). In addition, histochemical detection of $H_2O_2$ was performed by an endogenous peroxidase-dependent staining procedure using DAB (3,3'-diaminobenzidine) as described by Thordal-Christensen et al. (1997). The unripe fruits treated with PepEST protein were placed in a solution of 1 mg/ml DAB for 8 hr.

4. Assays for Gene Expressions

Total RNA was extracted by using Trizol reagent (Gibco BRL) according to the manufacturer's instructions. The equal amounts of total RNA (10 µg per lane) were separated on a 1.2% denaturing agarose gels in the presence of formaldehyde. RNA gel blotting, hybridization, and washing were conducted as described by the manufacturer of positively charged nylon membranes (Hybond $N^+$; Amersham Pharmacia Biotech). Radiolabeled probes were prepared with [$\alpha$-$^{32}$P] dCTP (3000 Ci/mmol, PerkinElmer), using redi-prime™ kit (Amersham Pharmacia Biotech). Membranes were washed twice with 2×SSPE, 0.1% SDS at 65° C. and once with 0.5×SSPE, 0.1% SDS at 65° C.

Probes for defense-related genes such as PR3 (Chitinase class II (CAChi2)), PR5 (Thaumatin-like protein (TLP)), PR10, PepThi, were used to examine their gene expression in pepper fruits by Northern hybridization or RT-PCR. The primer pairs used for the PCR analysis were PR3-5' (ATG GAG TTC TCT GTA TCA CCA GTG G) (SEQ ID NO: 3), 3' (TCC GAA TGT CTA AAG TGG TAC AAG) (SEQ ID NO: 4), PR5-5' (ATG GGC TAT TTG AGA TCA TCT) (SEQ ID NO: 5), 3' (TCA CCT CTC TGC AAT CAA TAT) (SEQ ID NO: 6), PR10-5' (CTG ACA AGT CCA CAG CCT CAG) (SEQ ID NO: 7), 3' (GTT CTT TCC ATG ACA ACC AAT TG) (SEQ ID NO: 8), Pepthi-5' (GGG GGA TCC AAA ATG GCT CGT TCC) (SEQ ID NO: 9), 3'(CTC GGT ACC CTT TAT TTA ATT TTG TGT GAC ACT) (SEQ ID NO: 10), respectively.

5. Induction and Purification of Recombinant PepEST Protein

A single colony of *E. coli* cells containing a recombinant pGEX6P-1 plasmid was picked to inoculate 5 ml of 2× YTA (Tryptone 16 g/l, Yeast extract 10 g/l, NaCl 5 g/l, Ampicillin 100 mg/l) medium and incubate for 12–15 hrs at 37° C. with vigorous shaking. Dilute the culture 1:100 into fresh prewarmed 2× YTA medium and grow at 37° C. with shaking until absorbance $A_{600}$ reaches 1.0. Then, 0.2 mM IPTG at the final concentration was added to the culture and continued the incubation for additional 3 hrs 30° C. Finally, the culture was centrifuged at 12,000 rpm for 10 minutes at 4° C. to sediment the cells. The supernatant was discarded. The cell pellet was completely suspended by adding 50 µl ice-cold 1× PBS per ml of culture medium. Suspended cells were disrupted using a sonicator on ice in short bursts. According to the manufacturer's instructions, the lysate was bound to Glutathione Sepharose 4B and then the fusion protein was treated with 80 U of Prescission protease in order to remove reduced GST from the PepEST protein. Protein content was determined by Bradford method (1979). SDS-PAGE was performed on 10% polyacrylamide gels.

To partially separate PepEST protein, the lysate was applied to 120 cm gel-filtration column (Sephadex G-150, Sigma). Separated proteins in No. 9 to 26 fractions were mixed, lyophilized, and dissolved in 1 mM dithiothreitol (DTT) before use.

6. Labelling of PepEST with FITC

Fluorescein isothiocyanate (FITC) was freshly dissolved in DMSO to 10 mg/ml and added to 1 mg/ml of purified PepEST protein in 100 mM sodium bicarbonate (pH 9.3) to final concentration of 1 mg/ml FITC. After incubation for 4 hrs in the dark at the room temperature, 1 M ethanolamine was added to inactivate the residual FITC. The solution was left in the dark for additional 2 hrs and applied for gel-filtration column chromatography using a 120 cm Sephadex G-50 (Sigma) column to remove unconjugated dyes. Separated samples are lyophilized. The conjugation between FITC and purified PepEST was verified on SDS-PAGE gel with intense fluorescence of purified PepEST under UV light.

7. A Rapid Method for Viability of Fungal Spores

To observe the viability of the fungus, Live/Dead® BacLight™ Bacterial Viability Kit (Molecular Probes) was used according to the manufacturer's instructions. Live/Dead consists of two reagents containing a mixture of fluorescent nucleic acid stains SYTO9 (green) and propidium iodide (red) in anhydrous DMSO.

8. Observation of Fungal Morphology by SEM (Scanning Electron Microscope)

Pepper fruits pieces were prepared for scanning electron microscope (SEM) after exogenous PepEST protein treatment. Small segments (5 mm long) were vacuum-infiltrated in sodium phosphate buffer (pH 7.0) containing 2% sucrose, 3% paraformaldehyde and 0.2% glutaraldehyde on ice for 6 hrs. Following this treatment, the material was slowly dehydrated in a graded ethanol series at room temperature. After the last change of ethanol, the samples were immediately submitted to critical point drying, gold coated, and observed with a scanning electron microscope (Hitachi).

9. Treatment of FITC-Labeled Concavanalin A (ConA)

Fluorescein isothiocyanate-labeled ConA (Sigma) was used to examine the surface structure of the fungus after the treatment of PepEST protein. Germinated fungi were treated with 0.1 mg/ml FITC-ConA in PBS and examined under a fluorescence microscope (Olympus).

EXAMPLES

Example 1

Purification of Recombinant PepEST Protein

Figure 1:
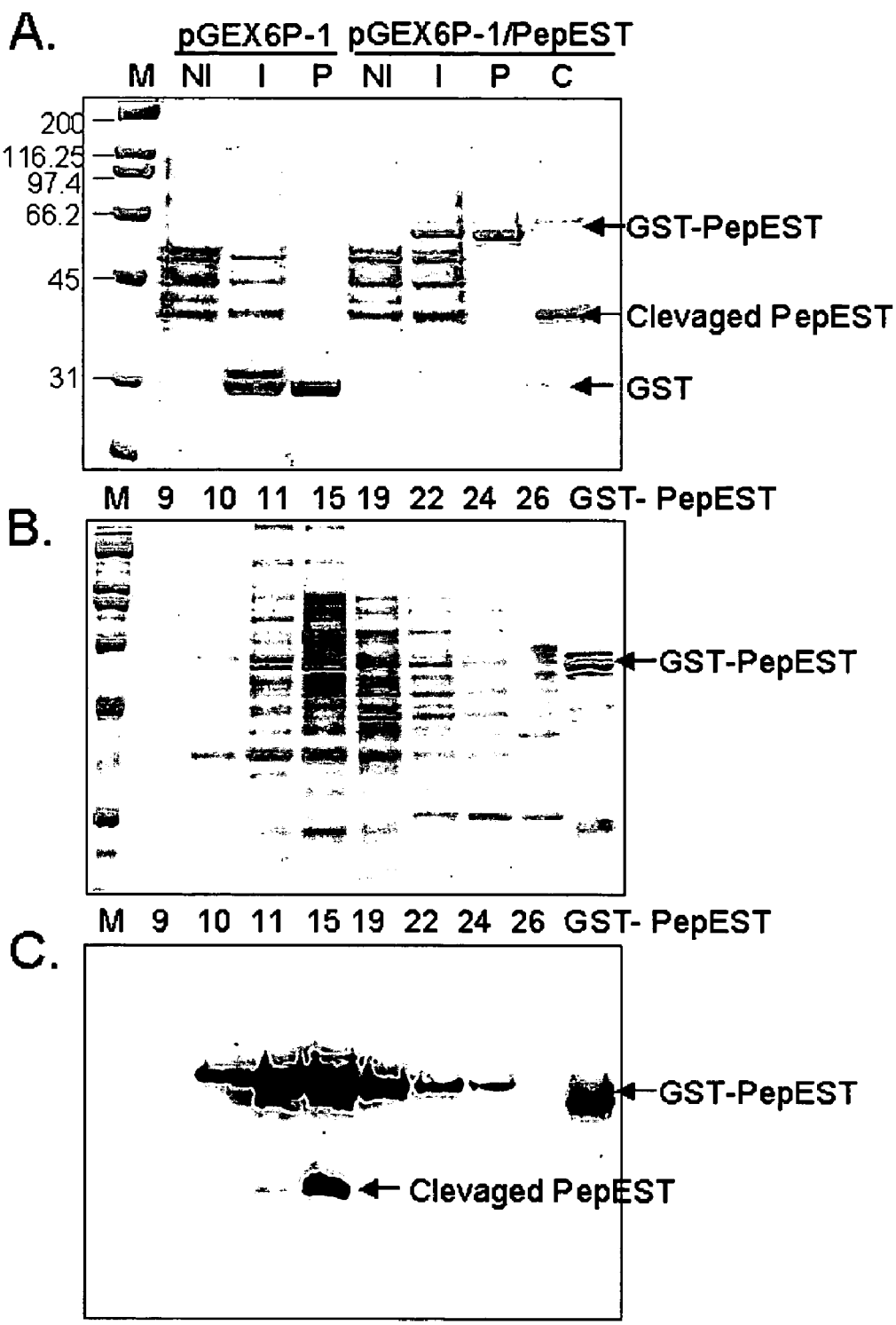
FIG. 1 shows the SDS-PAGE analysis of recombinant PepEST protein produced in *E. coli* carrying pGEX6p-1/PepEST (A), fraction No. 9 to 26 after size fractionation of soluble proteins from the *E. coli* carrying pGEX6p-1/PepEST (B), western analysis of same fractions in B showing PepEST protein bands (C).

The open reading frame of PepEST cDNA (AF122821) was inserted in-frame with the glutathion-S-transferase (GST) coding sequence in expression vector, pGEX6P-1 between EcoRI and XhoI sites. The GST-PepEST fusion protein was expressed in E. coli and then purified. FIG. 1A shows that 63.5 KD GST-PepEST fusion protein is cleaved with GST protein resulting a 36.5 KD PepEST protein. To partially separate PepEST protein, the lysate was applied to 120 cm gel-filtration column (Sephadex G-150, Sigma). In FIG. 1B, Separated proteins in No. 9 to 26 fractions were separated on SDS-PAGE. And PepEST protein was detected by western blotting in the same fraction (FIG. 1C).

Example 2

Solubilization of Cutin Monomer

The cuticle is the outer protective layer, which covers the aerial part of higher plant. To penetrate into the underlying epidermis, fungus used an enzyme hydrolyzing plant cuticles. It has been reported that degradation products from the cuticle could activate defense reaction in the host plants. In the present experiment, PepEST protein was topically applied on healthy unripe pepper fruit to clarify possible involvement of the degradation compound from cuticles. As the result, glycerol and 9-octadecenamide was released from the cuticle of the fruit treated with PepEST protein (FIG. 2).

Example 3

Generation of Hydrogen Peroxide in Pepper Cells

To demonstrate the effect of PepEST protein on plant cells, generation of $H_2O_2$ was examined as a parameter for defense and induction of defense related genes in the unripe fruit treated with PepEST protein. In FIG. 3A, the results show that the application of distilled water on the unripe fruit as control did not affect hydrogen peroxide generation. However, dark brown precipitates were homogenously detected in the epidermal cells of unripe fruit treated with PepEST protein for 6 hrs. To examine the time-course of differential accumulation of $H_2O_2$ by PepEST protein, the amount of hydrogen peroxide was measured during a day after the treatment. The accumulation pattern of $H_2O_2$ associated with PepEST treatment was quantitatively, but not qualitatively distinguishable from the application of distilled water as control (FIG. 3B). Generation of $H_2O_2$ was induced biphasically at 0.5 and 6 hrs after the treatment. Generation of $H_2O_2$ was significantly higher in the fruit treated with PepEST protein than the control.

Example 4

Expression of Defense-Related Genes in Pepper Cell

To test whether PepEST protein induces PR gene expression, RNA blot analysis was performed on unripe fruits after treatment with PepEST protein. Also, we examined the level of PR gene transcripts in unripe fruits after treatment with hydrogen peroxide as $H_2O_2$ is known to elicit resistance reaction in plants. PR genes such as PR3, PR5, PR10 and PepThi were induced in the fruits treated with hydrogen peroxide (FIG. 4). PR3 and PR5 were strongly induced from the early stage of incubation and then gradually decreased. In contrast, the transcripts of PR10 were strongly induced with time. Upon PepEST protein treatment, expression of PR genes showed similar patterns with those induced by hydrogen peroxide, but their level of expression slightly decreased, except for PepThi whose transcripts accumulated at 6 hrs after treatment.

Treatment of the unripe pepper with PepEST protein led to the induction of defense related genes in the absence of the fungal pathogen, suggesting that PepEST protein induced resistance protects pepper fruits from the fungal pathogen. To investigate whether the induction of PR genes occurs in infected fruits with anthracnose fungus, the expression pattern of PR genes was monitored in the treated fruits after inoculation of fungal spores. FIG. 5 shows that the transcripts corresponding to PR5 and 10 genes accumulated only in the treated fruits at 72 hrs after inoculation.

Example 5

Inhibition of Fungal Development by PepEST Treatment

The conidia of C. gloeosporioides started to germinate at 1 hr after deposition on the surface of unripe pepper fruits or cover glass. One conidium produced a germination tube with swollen tip forming an appressorium. First apressorium developed at 6 hrs. However, normal development of the fungus was severely impaired by the application of PepEST recombinant protein. FIG. 7A shows an abnormal development of the fungus treated with PepEST protein on cover glass at 24 hrs. At low concentrations of PepEST protein, the growing tip of hypha tended to elongate and sometimes produced new spores without developing appressorium. The growth of fungus was completely blocked at 0.5 mg/ml of PepEST.

Viability of the fungus showing an abnormal growth pattern was examined by staining with Live/Dead®

BacLight™ Bacterial Viability Kit based on two-color fluorescence assay of cell viability. The stains have different spectral characteristics and differ in their ability to penetrate fungal cell membranes. Cells with intact membranes labeled with green fluorescence, whereas cells with damaged membranes stained fluorescent red. The results show that viability of the fungus was severely affected even at low concentration of PepEST protein (FIG. 6).

In addition, fungal morphology on the unripe pepper fruit was observed by using a scanning electron microscope (Hithachi). The spores of C. gloeosporioides were inoculated on the unripe pepper fruits with PepEST protein and then incubated for 24 hrs. Fungal growth proceeded as usual with distilled water as control and germination tube with appressorium was observed (FIG. 7A). By treating with 1 µg of PepEST protein, appressorium did not develop on the fungus, and the fungus showed severe abnormality at 5 µg of the protein.

Example 6

Surface Damage of the Fungus after Exogenous Treatment with PepEST Protein

To observe celullar localization of PepEST protein, PepEST protein was labeled with FITC as described above (FIG. 8A). GST protein was used as a control. The GST-FITC protein accumulated inside the fungal cells after 24 hrs of incubation. The growth and differentiation of the spores were not affected at all. However, PepEST-FITC protein did attach to the outer surface of hypha (FIG. 8B).

Since PepEST protein is a hydrolytic enzyme with esterase activity, the surface of the fungus treated with the protein was examined by both fluorescence and scanning electron microscopes. Labeling of cell walls with ConA-FITC resulted in an even fluorescence on the outside walls of the fungus germinated in distilled water as control. However, the labeled walls of the fungus treated with PepEST protein appear severely altered. The PepEST protein induced change in cell wall morphology indicates that PepEST protein dissolves the materials deposited on the outside of the walls (FIG. 9A). To determine whether PepEST protein hydrolyzes the cell wall, ultrastructure of the affected fungus surface was observed with a Field-Emission Scanning Electron Microscope (Hitachi). The surface of the fungal wall was covered with undefined mucilage materials in distilled water, but the skeletons of the wall structure was exposed after the treatment with PepEST protein (FIG. 9B). Decomposed materials from the treated fruits were analyzed using GC-mass spectrometry. Two compounds were detected in the digested solution, glycerol and 1,2-dithiane-4,5-diol (FIG. 10).

Example 7

Protection of the Unripe-Green Pepper Fruit Cells

By application of pepEST protein in a dose-dependent manner, the fungal appressorium formation was significantly inhibited in the infected fruits with the anthracnose fungus. Blocking of the appressorium development resulted in protection of the unripe fruit against the fungus (FIG. 11). The epidermal cells of pepper fruit remained healthy in the treated fruits at 72 hrs after inoculation with fungus while the fungus penetrated into the epidermal cells of untreated fruits.

Example 8

A Formula Comprised of PepEST Protein

Soluble proteins containing PepEST protein were separated by size fractionation. Fraction No. 9 to 26 containing the protein were mixed together. PepEST protein accounted for 1% of the separated protein fractions. The resulting protein mixture was lyophilized and dissolved in distilled water to 250 µg per milliliter of final concentration. Then, DTT was added to the protein solution to 1 mM of final concentration, designated as formulaKH1.

When the spores of anthracnose fungus were treated with formulaKH1, spore germination was completely inhibited as shown in FIG. 12.

REFERENCES

Baudouin E, Charpenteau M, Roby D, Marco Y, Ranjeva R, Ranty B (1997) Functional expression of a tobacco gene related to the serine hydrolase family. Esterase activity towards short-chain dinitrophenyl acylesters. Eur J Biochem 248, 700–706

Contreras J A, Karlsson M, Osterlund T, Laurell H, Svensson A, Holm C (1996) Hormone-sensitive lipase is structurally related to acetylcholinesterase, bile salt-stimulated lipase, and several fungal lipases. J Biol Chem 271, 31426–31430

Daykin 1984

Dodd et al. 19

Falk A, Feys B J, Frost L F, Jones J D G, Daniels M J, Parker J E (1999) EDS1, and essential component of R gene-mediated disease resistance in Arabidopsis has homology to eukaryotic lipases. Proc Natl Acad Sci 96, 3292–3297

Feller G, Thirty M, Gerday C (1991) Nucleotide sequence of the lipase gene lip2 from the Antarctic psychrotroph Moraxella TA144 and site-specific mutagenesis of the conserved serine and histidine residues. DNA Cell Biol 10, 381–388

Huang A H C (1987) Lipases. The Biochemistry of Plants 9, 91–119

Jirage D, Tootle T L, Reuber T L, Frost L N, Feyes B J, Parker J E, Ausubel F M, Glazebrook J (1999) Arabidopsis thaliana PAD4 encodes a lipase-like gene that is important for salicylic acid signaling. Proc Natl Acad Sci 96, 13583–13588

Kim Y S, Lee H H, Ko M K, Song C E, Bae C Y, Oh B J (2001) Inhibition of fungal appressorium formation by pepper (Capsicum annuum) esterase. Mol Plant-Micro Interaction 14, 80–85

Kok R G, Christoffels V M, Volsman B, Hellingwerf K J (1993) Growth-phase-dependent expression of the lipolytic system of Acinetobacter calcoaceticus BD413: Cloning of a gene coding one of the esterase. J Gen Microbiol 139, 2329–2342

Langin D, Laurell H, Stenson-Holst L, Belfrage P, Holm C (1993) Gene organization and primary structure of human hormone-sensitive lipase: Possible significance of a sequence homology with a lipase of Moraxella TA144, an Antarctic bacterium. Proc Natl Acad Sci 90, 4897–4901

Liyama K, Lam T B, and Stone B A (1994) Covalnet Cross-Links in the Cell Wall. Plant Physiol 104, 315–320

Oh B J, Kim K D, Kim Y S (1998) A microscopic characterization of the infection of green and red pepper fruits by an isolate *Colletotrichum gloeosporioides*. J Phytopathol 146, 301–303

Oh B J, Kim K D, and Kim Y S (1999a) Effect of cuticular wax layers of green and red pepper fruits on infection by *Colletotrichym gloeosporioides*. J Phytopathol 147, 547–552

Oh B J, Ko M K, Kim Y S, Kim K S, Kostenyuk I, Kee H K (1999) A cytochrome P450 gene is differentially expressed in compatible and incompatible interactions between pepper (*Capsicum annuum*) and anthracnose fungus, *Colletotrichum gloeosporioides*. Mol Plant Microbe Inter 12, 1044–1052

Osterlund T, Contreras J A, Holms C (1997) Identification of essential aspartic acid and histidine residues of hormone-sensitive lipase: Apparent residues of the catalytic triad. FEBS Lett 403, 259–262

Patterson B D, Macrae E A, Ferguson I B (1984) Estimation of Hydrogen Peroxide in Plant Extracts Using Titanium (IV). Analytical Biochemistry 139, 487–492

Pontier D, Godlard L, Marco Y, Roby D (1994) hsr203J, a tobacco gene whose activation is rapid, highly localized and specific for incompatible plant/pathogen interactions. Plant J 5, 507–521

Schoffelmeer E A M, Klis F M, Sietsma J H, Cornelissen B J C (1999) The Cell Wall of *Fusarium oxysporum*. Fungal Genetics and Biology 27, 275–282

Thordal-Christensen H, Zhang Z, Wei Y, Collinge D (1997) Subcellular localization of $H_2O_2$ in plants. $H_2O_2$ accumulation in papillae and hypersensitive response during the barley-powdery mildew interaction. Plant 11, 1187–1194

Warm E and Laties G (1982) Quantification of Hydrogen Peroxide in Plant Extracts by the Chemiluminescence Reaction with Luminol. Phytochemistry 21, 827–831

What is claimed is:

1. A biocontrol agent comprising 0.05–0.2 mg per milliliter of an effective amount of pepper esterase (PepEST) having amino acid sequence of SEQ ID NO: 1, wherein said pepper esterase induces the protection mechanism of plant by releasing cutin monomer, generating hydrogen peroxide and expressing pathogenic related (PR) genes.

2. The biocontrol agent according to claim 1, wherein cutin monomer is released by hydrolyzing cuticles from the unripe pepper fruit.

3. The biocontrol agent according to claim 2, wherein said cutin monomer is 9-octadecenamide.

* * * * *

UNITED STATES PATENT AND TRADEMARK OFFICE
CERTIFICATE OF CORRECTION

PATENT NO. : 6,998,120 B2 Page 1 of 1
APPLICATION NO. : 10/848375
DATED : February 14, 2006
INVENTOR(S) : Kim et al.

It is certified that error appears in the above-identified patent and that said Letters Patent is hereby corrected as shown below:

| Column | Line | |
|---|---|---|
| 1 | 31 | Change "casual agent" to -- causal agent --; |
| 2 | 13 | Change "repectively" to -- respectively --; |
| 2 | 21 | Change "agromonically" to -- agronomically; |
| 2 | 31 | Change "mililiter" to -- milliliter --; |
| 2 | 52 | Change "purfied" to -- purified --; |
| 2 | 65 | Change "(C)" to -- (C) --; |
| 3 | 53 | Change "detestable" to -- detectable --; |
| 4 | 15 | Change "Iiyama" to -- Liyama --; |
| 6 | 44 | Chage "Prescission" to -- PreScission™ --; |
| 7 | 35 | Change "glutathion" to -- glutathione --; and |
| 9 | 25 | Change "celullar" to -- cellular --. |

Signed and Sealed this

Seventeenth Day of October, 2006

JON W. DUDAS
*Director of the United States Patent and Trademark Office*